United States Patent [19]

Benardella

[11] Patent Number: Plant 6,569

[45] Date of Patent: Jan. 31, 1989

[54] ROSE PLANT NAMED BENRAD

[75] Inventor: Frank A. Benardella, Old Tappen, N.J.

[73] Assignee: Nor'East Miniature Roses, Inc., Rowley, Mass.

[21] Appl. No.: 62,067

[22] Filed: Jun. 15, 1987

[51] Int. Cl.[4] ..... A01H 5/00

[52] U.S. Cl. ..... Plt./10

[58] Field of Search ..... Plt./10

*Primary Examiner*—Robert E. Bagwill
*Attorney, Agent, or Firm*—Vincent G. Gioia

[57] ABSTRACT

A new unusual orange red miniature rose variety.

1 Drawing Sheet

The present invention relates to a new and distinct variety of rose plant of the miniature rose class, which was originated by my crossing as seed parent the rose known as "Sheri Anne" and as pollen parent the rose known as "Sheri Anne". The denomination of this new rose is "Benrad".

Among the novel characteristics possessed by this new variety which distinguish it from its parents and all other varieties of which I am aware are its well formed orange red flowers which are long lasting on the plant and after cutting. Asexual reproduction by budding of the new variety as performed in San Bernardino County, Calif., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Colour Chart (RHSCC). The terminology used in color description herein refers to plate numbers in the aforementioned color chart, e.g., "42A" is plate 42A of the Royal Horticultural Society Colour Chart.

Parentage: Seedling.
*Seed parent.*—"Sheri Anne".
*Pollen parent.*—"Sheri Anne".
Class: Miniature.

The following observations are made of specimens grown outdoors in San Bernardino County, Calif., during the month of April.

FLOWER

Blooming habit: Recurrent.

A. Bud:
(1) *Size.*—Medium.
(2) *Form.*—Pointed, ovoid.
(3) *Color.*—After sepals fall, bud color is between 42A and 42B.
(4) *Sepals.*—Slightly longer than bud, minimum foliation.
(5) *Peduncle.*—Length — about 1⅝ inch. Aspect — straight. Strength — erect. Color — near 146D.

B. Bloom:

(1) Size.—Average size when fully expanded — about 1¾ inches.
(2) *Borne.*—Primarily singly, one to a stem.
(3) *Form.*—Well formed flowers high centered at first, becoming flat. Outer petals reflex and quill to points; inner petals roll under. Before flower becomes fully open, outer petals tend to have pointed apices.
(4) *Petalage.*—Number of petals under normal conditions — about 23–27.
(5) *Color.*—After sepals fall and petals unfurl, flowers appear orange red in coloring, between 42A and 42B. Petals show deeper toned veining which becomes more pronounced as flower matures. In open blooms, petals lighten becoming near 47D to B, with the lighter tones toward petal edges. Flower centers in open blooms are near 25D with near white stigmas also visible.

C. Petals:
(1) *Texture.*—Average.
(2) *Appearance.*—Inside velvety and outside satiny.
(3) *Form.*—Fan shaped.
(4) *Arrangement.*—Regularly arranged.
(5) *Petaloids in center.*—Few.
(6) *Persistence.*—Drop off cleanly.
(7) *Fragrance.*—Slight.
(8) *Lasting quality.*—Long lasting quality on plant and as cut flower.

REPRODUCTIVE ORGANS

A. Stamens, filaments and anthers:
*Arrangement and color.*—Regularly arranged around styles. Color — filaments near 21B.

B. Pollen:
*Color.*—Near 25D.

C. Styles: Medium, even.

D. Stigmas:
*Color.*—Near 11C.

E. Hips: None observed.

PLANT

A. Form: Upright.

B. Growth: Very vigorous.
*Height attained.*—About 18–30 inches.

C. Foliage: Compound 5 to 7 leaflets.
(1) *Size.*—Large for miniature.
(2) *Quantity.*—Abundant.
(3) *Color.*—New foliage: Upper side — near 146B. Under side — near 146C. Old foliage: Upper side — near 139A. Under side — near to 148C.

(4) *Shape.*—Ovate, pointed.

(5) *Texture.*—Upper side is semiglossy; under side is matte.

(6) *Edge.*—Serrate.

(7) *Serration.*—Ordinary.

(8) *Leaf stem.*—Color — near to 141A. Under side — near 146D.

(9) *Stipules.*—Medium, not bearded.

(10) *Resistance to disease.*—Blackspot — Average. Mildew — Average. Rust — Average.

D. Wood:

(1) *New wood.*—Color — near 146B. Bark — smooth.

(2) *Old wood.*—Color — near 147B. Bark — smooth.

E. Thorns:

(1) *Thorns.*—Quantity (main stalk) — ordinary. On laterals from stalk — ordinary. Form — long, thin, straight, angled slightly downward. Length — medium. Color — near 182B. Position — irregular.

(2) *Prickles.*—None.

F. Winter hardiness: Needs protection in severe climate.

I claim:

1. A new and distinct variety of rose plant of the miniature rose class, substantially as shown and described, characterized particularly by well-formed orange red flowers which open well and which are long lasting on the plant and as cut flowers.

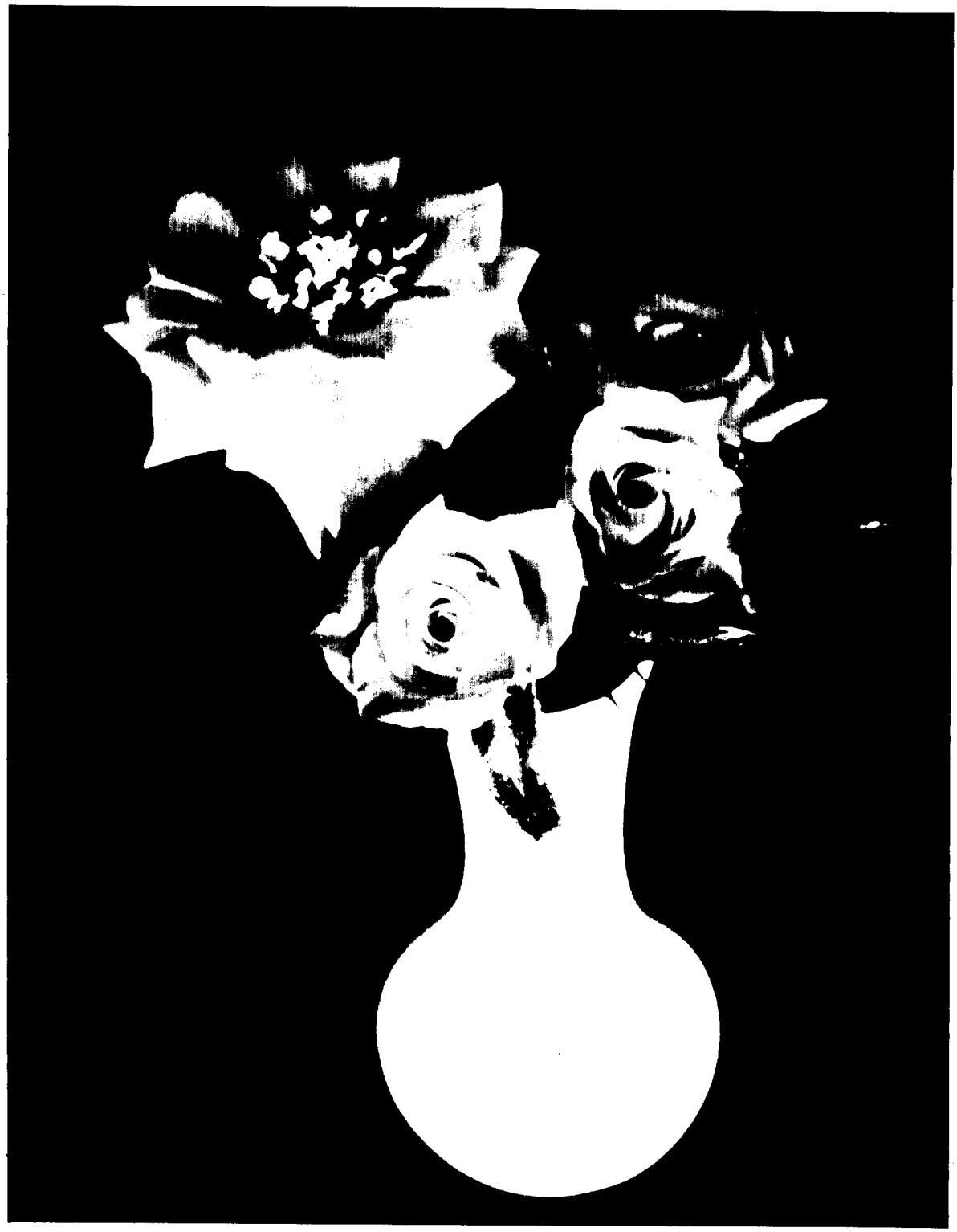

* * * * *